(12) United States Patent
Hahn et al.

(10) Patent No.: US 6,423,801 B1
(45) Date of Patent: Jul. 23, 2002

(54) BRANCHED POLYAMMONIUM COMPOUNDS OF HIGH MOLECULAR WEIGHT AND PROCESSES FOR PRODUCING SAID COMPOUNDS

(75) Inventors: Mathias Hahn, Wilhelmshorst; Werner Jaeger, Kleinmachnow, both of (DE); Jeffrey R. Cramm, Batavia, IL (US)

(73) Assignee: Nalco Chemical Company, Naperville, IL (US)

( * ) Notice: Subject to any disclaimer, the term of this patent is extended or adjusted under 35 U.S.C. 154(b) by 0 days.

(21) Appl. No.: 09/029,002
(22) PCT Filed: Jul. 8, 1996
(86) PCT No.: PCT/DE96/01275
§ 371 (c)(1), (2), (4) Date: Feb. 8, 1999
(87) PCT Pub. No.: WO97/03099
PCT Pub. Date: Jan. 30, 1997

(30) Foreign Application Priority Data

Jul. 7, 1995 (DE) .......................................... 195 24 867

(51) Int. Cl.$^7$ ................................................ C08F 26/06
(52) U.S. Cl. ........................ 526/258; 525/291; 525/293; 525/296; 525/301; 525/303
(58) Field of Search ................................. 525/291, 293, 525/296, 301, 303, 308; 526/258

(56) References Cited

U.S. PATENT DOCUMENTS

| 5,128,041 | A | * | 7/1992 | Degen et al. ................ 210/638 |
| 5,200,086 | A | * | 4/1993 | Shah et al. .................. 210/708 |
| 5,211,854 | A | * | 5/1993 | Liao et al. ................... 210/734 |
| 5,512,636 | A | * | 4/1996 | Polizzotti et al. ........... 525/285 |

FOREIGN PATENT DOCUMENTS

| EP | 0353987 | * | 7/1990 | ............ A61K/7/00 |
| JP | 63242309 | * | 7/1988 | ........... B01D/21/01 |

* cited by examiner

Primary Examiner—David W. Wu
Assistant Examiner—Tatyana Zalukaeva
(74) Attorney, Agent, or Firm—Michael B. Martin; Thomas M. Breininger

(57) ABSTRACT

The invention is concerned with water soluble high-molecular weight quaternary ammonium graft polymer, wherein ammonium salt side chains are grafted onto a polyamine backbone under free radical conditions, and wherein the initiator system comprises a free radical-producing oxidizing agent and the polyamine backbone polymer.

9 Claims, No Drawings

BRANCHED POLYAMMONIUM COMPOUNDS OF HIGH MOLECULAR WEIGHT AND PROCESSES FOR PRODUCING SAID COMPOUNDS

This is a 371 of International Patent Application No. PCT/DE96/01275, filed Jul. 8, 1996.

The present invention concerns novel water-soluble polyammonium salts, branched in a specific way, with high molecular weight and a process for their preparation. Such polymers are useful in water purification processes.

The increasing application of water-soluble, cationic polymers and copolymers in methods for waste water treatment, such as the dewatering of sludge or purification of contaminated water is leading to new developments in the area of synthesis of new types of polyammonium salts.

The effectiveness of using highly cationic polymers depends on the molecular weight of the polymer, on the nature of the selected monomer and on the architecture of the polymer chain.

The synthesis of water-soluble, polymeric, quaternary ammonium salts by free-radical polymerization is known and leads to linear polymer structures. An example of this is the solution polymerization of diallyldimethylammonium chloride (DADMAC), which is described in U.S. Pat. No. 3,288,770 or in DD Patent 127,729.

In order to obtain special product properties or to synthesize polymers with higher molecular weight, copolymerization with polyfunctional crosslinking comonomers are used. Mixtures of the ammonium monomer with bisallyl esters of dicarboxylic acids are polymerized in aqueous solution with free-radical initiation (DD Patents 127,729, 128,189 or 128,247). Such branched structures are also obtained in agreement with the teaching of FR Patent 1,494,438 or U.S. Pat. No. 3,544,318. Here, triallyl- or tetraallylammonium salts are used as chain-branching agents. The necessary small amounts of chain-branching agents are added to the batch at the beginning of the polymerization. It is well known that at concentrations of the polyfunctional monomer of more than 0.1%, the obtained polymer is partially or completely crosslinked. This leads to a polymer which is insoluble in the solvent (Vollmert, Grundriss der Makromolekularen Chemie, Springer-Verlag, Berlin, 1962,p. 196). In EP Patent 0,264,710, an improved method is presented for the copolymerization of DADMAC with such polyfunctional monomers. If a dosage method is used for the comonomer, the comonomer can be incorporated to a greater extent. In this way, polymers with higher molecular weight are obtained and the risk of gelling during the polymerization is reduced. In general, a fairly complicated addition program must be followed in order to obtain a successful polymerization result.

In all cases in which polyfunctional, crosslinking comonomers are used as agents for increasing the molecular weight, there is still a processing risk because of the possibility of gel formation. On the other hand, one cannot avoid producing, in addition to highly branched polymer chains with high molecular weight, macromolecules with a lower degree of polymerization. Because of the reduced activity in practical applications of the poly-ammonium salt, the fraction with low-molecular weight is disadvantageous.

Branched polymers can also be synthesized by a graft copolymerization method. This method was also used for the synthesis of DADMAC-acrylamide copolymers (G. B. Butler, J. Macromol. Sci. A26, 681 (1989)). A copolymer of DADMAC and dihydroxyalkyl derivatives of acrylic acid is synthesized as a prepolymer and then, using $Ce^{4+}$ salts as initiator, free-radical grafting of acrylamide or a mixture of acrylamide and DADMAC onto the prepolymer is achieved. In all cases, high concentrations of the prepolymer are needed in order to obtain polymer yields of about 80%. This is unacceptable from an industrial point of view.

Branched copolymers of acrylamide and cationic monomers, such as cationic, modified acrylate esters or acrylamides or diallylammonium salts are synthesized in a similar way by copolymerization of acrylamide with macromonomers of the cationic functionalized monomer having a double bond as the terminal group, as described in U.S. Pat. No. 5,211,854.

It is the task of the present invention to develop novel, water-soluble polymers, quaternary ammonium salts with DADMAC in particular as repeating unit of the polymer chain, which are characterized by a comb-like structure, in which the DADMAC-amine copolymer or any other water-soluble polyamine containing charged units represents the rigid backbone chain and the quaternary ammonium salt, preferably DADMAC, is arranged as chain units in side chains suspended on the backbone. Another task is to propose a method for their preparation.

The task is solved with regard to the polyammonium salt by the characterizing features of claim 1 and with reference to the method by the characterizing features of claim 8. The Subclaims show advantageous further developments.

The branched polyammonium salt with high-molecular weight according to the invention consists of unsaturated quaternary ammonium compounds and suitable prepolymers containing linear amine groups, in which the prepolymer represents the backbone and the ammonium salt forms the side chain. In the polyammonium salt according to the invention, 0.1 to 30 mole % of the prepolymer sequence–$[A—B—NR]_n$—represents the backbone and 70 to 99.9 mole % of the quaternary ammonium salt represents the side chain. The prepolymer sequence that forms the backbone chain is selected from polyampholytes, copolymers of diallyldimethylammonium chloride and a polymerizable amine compound, polyamideamine and DADMAC. The quaternary ammonium salt is attached as chain element to the amine-group-containing prepolymer. The comb-like branched polyammonium salt can be represented by the following general formula I:

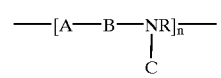

where C represents the quaternary ammonium salt side chain.

The comb-like polyammonium salt has a degree of polymerization which is chosen in such a way that a molecular weight >100,000, preferably >250,000 g/mole results. The degree of polymerization n of the prepolymer is chosen so that a molecular weight of the linear, amine-group-containing prepolymer is in the range between 10,000 and 100,000 g/mole.

It is preferable when the amine-group-containing prepolymer sequence is chosen from compounds having the following formulas 2 to 4:

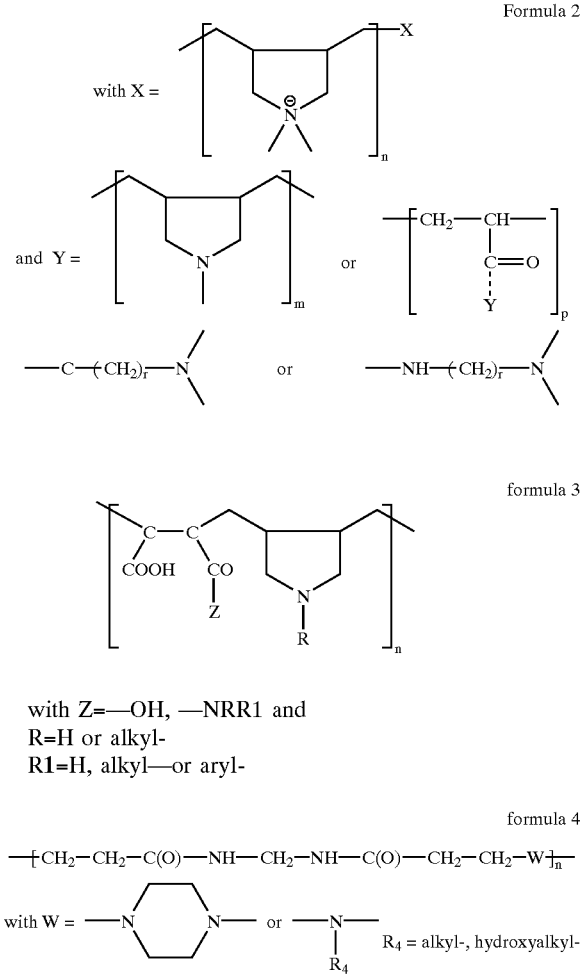

with Z=—OH, —NRR1 and
R=H or alkyl-
R1=H, alkyl—or aryl-formula 4

—[CH$_2$—CH$_2$—C(O)—NH—CH$_2$—NH—C(O)—CH$_2$—CH$_2$—W]$_n$— with W = —N\_/N— or —N— , R$_4$ = alkyl-, hydroxyalkyl-
                         |
                         R$_4$ In the preferred prepolymers of general formula 2, the degree of polymerization n, m and n, p is chosen in such a way that a molecular weight of 10,000 to 100,000 g/mole results, where the ratio n:m and n:p is in the range from 1:1 to 95:1.

Furthermore, it is preferable when the prepolymer is a DADMAC polymer with 0.5 to 5 mole % of triethanolamine units.

The novel, water-soluble, comb-like, polymeric, quaternary ammonium salts are polymers based on unsaturated quaternary ammonium salts and especially DADMAC, as well as on a suitable water-soluble prepolymer that consists of at least 1 mole % to 100 mole % of amine function-containing compounds as repeating unit in the rigid prepolymer chain.

Futhermore, the invention is concerned with a method for the preparation of a water-soluble high molecular weight quaternary ammonimn graft polymer wherein quaternary ammonium salt side chains are grafted onto a polyamine backbone polymer under ree radical conditions, wherein the initiator system comprises a free radical-producing oxidizing agent and the polyarine backbone polymer. Preferably, the polymerization is carried out with 30–65 weight percent solutions in water of the monomer at temperatures of 15–65° C., wherein the polyamine backbone consists of 1–100 mole percent amine function containing units and wherein the polyamine backbone polymer has a molecular weight of 10,000 to 100,000 g/mole.

When using the present invention, novel, comb-like polyammonium salts with average molecular weights of >100,000, preferably 250,000 and even more preferably >500,000 g/mole are obtained; in addition, the prepolymer is completely embeded in the final polymer and the amount of homopolymer is insignificantly small.

Due to the new comb-like architecture, which consists of the rigid polyamine-group-containing backbone and cationic attached macromolecular side chains, the obtained novel copolymers differ from the polyammonium salts of the state of the art by a number of characterizing properties. The fundamental structure of the prepolymer can be detected in the final product. It is possible to control the molecular weights of the copolymers by the molecular weights and the concentration of the grafting points of the prepolymer. Furthermore, the number of attached chains can be controlled by the concentration of the graftable functional groups in the prepolymer. In this way, there is a great variation in order to adapt the properties of the comb-like polyelectrolytes in solution (the solution property is the significant interaction parameter for industrial applications of these polymers).

The drastic increase of the intrinsic viscosities during polymerization is also a characteristic property of the novel polymers. For DADMAC as cationic monomer of the polymer synthesis of the present invention, the copolymers are characterized by being insoluble in methanol.

The following examples refer to the polymerization of DADMAC as an example of a typical cationic monomer. They are not considered to represent a limitation to the exclusive use of this monomer for the present invention.

EXAMPLE 1

In a 1 L glass reactor, which is equipped with an anchor stirrer made of stainless steel, 200 g of a 60% aqueous solution of DADMAC is mixed with 6 g of a 50% aqueous solution of an additional product of methylene-bis-acrylamide and diethylenediamine (MBAAPIP, the amount of polyamine corresponds to an amine concentration of 0.07 mole/L). The temperature of the mixture was adjusted to 25° C. and then nitrogen gas was blown through it for 30 minutes. The pH of the solution was then adjusted to 9.5 by the addition of NaOH before the addition of 0.9 g of ammonium persulfate (0.02 mole/L) within 15 minutes as a 10% solution in water. The reaction mixture was kept at this temperature for 8 hours at a stirrer speed of 30 mn$^{-1}$. Then 100 g of water was added and the mixture was heated to 65° C. Then another 0.25 g of ammonium persulfate was added and the reaction temperature was kept constant for another 60 minutes. The reaction mixture was diluted with water to a solid concentration of 20% and cooled to room temperature. The polymerization conversion reached 97.5%, as determined by $^1$H-NMR. The relative viscosity of a 1% solution of the isolated polymer in 1 N NaCl was found to be 8.54.

EXAMPLE 2–4

The same method was performed as in Example 1 but different polyamine compounds were used. The following polyamine compounds were employed:
Example 2: Copolymer of DADMAC and diallylmethylamine with 10 mole % of amine groups (DADMACDAMA);
Example 3: alternating copolymer of N-butylmaleic acid and diallylmethylamine (BUMAS-DAMA);
Example 4: poly-DADMAC, which contains 3 mole % of triethanolamine units (DAD-MACTEA).

The same initiator concentration (0.02 mole/L) was used and, in consideration of the fact that the initial reaction mixtures are different in the different experiments, the amounts of water added were adjusted to the condition of Example 1.

The results of these polymerization examples are listed in Table 1.

TABLE 1

DADMAC polymerization with different polyamine compounds

| polyamine | amount/g | conversion/% | relative viscosity |
|---|---|---|---|
| DADMACDAMA | 59 (50% solid) | 96.5 | 4.42 |
| BUMASDAMA | 9.8 (50% solid) | 98.5 | 7.82 |
| DADMACTEA | 233 (40% solid) | 98 | 6.95 |

EXAMPLE 5

In a 1 L glass reactor, which was equipped with a rotary agitator, 400 g of 60% DADMAC solution was mixed with 450 g of a 40% solution of DADMACTEA. After blowing nitrogen gas through the mixture for 30 minutes, the pH was adjusted to 9 with the addition of NaOH and 0.02 mole/L of ammonium persulfate was added at a stirrer speed of 30 $\text{min}^{-1}$. When the viscosity of the reaction mixture reached a stirrer torque of 1000 mNm as a result of the progress of polymerization conversion, 40 g of water was added to the reaction mixture. The reaction was continued under these conditions until the stirrer torque reached 1000 mNm again. Then, 40 g of water was added again. A total of six such cycles were performed. After the last addition of the water, the limiting value of the stirrer torque was no longer reached and, after a reaction time of 8 hours, the reaction mixture was diluted to 30% by the addition of 160 g of water, heated to 65° C. and another $5\times10^{-3}$ mole/L of ammonium persulfate were added. The reaction was maintained for another 60 minutes before the polymer solution was cooled to room temperature. A polymerization conversion of 98.5% was obtained (determined by $^1$H NMR) and the viscosity measurement of the 1% solution of the isolated polymer in 1 N NaCl gave a relative viscosity of 10.02.

EXAMPLES 6 and 7

These examples describe the progressive branching of the macromolecular chains during the polymerization conversion and the influence of the amine-persulfate ratio on chain branching.

The polymerization was carried out according to Example 1. An alternating copolymer based on morpholine-maleic acid and diallylmethylamine was used as the polyamine compound. The concentration of ammonium persulfate was chosen to be $2\times10^{-2}$ mole/L in both comparative experiments, but the polyamine concentration was varied. In Example 7, $1\times10^{-2}$ mole/L of polyamine compound was used and in Example 8, $7\times10^2$ mole/L was used. At the times at which the polymerization conversions remained comparable in the two experiments, samples were taken from the progressing polymerizations. The values of the polymerization conversions, the intrinsic viscosities and the determined stoichiometric coefficients of the simplex titration with polyacrylic acid are listed in Table 2.

TABLE 2

Polymerization results of DADMAC polymerization with N-morpholine maleic acid as polymeric amine compound

| polymerization example | polymerization conversion, % | intrinsic viscosity/dL/g | stoichiometric coefficient |
|---|---|---|---|
| Example 6 | 16 | 1.239 | 0.68 |
|  | 41.5 | 1.300 | 0.70 |
|  | 95 | 1.380 | 1.60 |
| Example 7 | 23 | 0.942 | 0.72 |
|  | 43 | 1.148 | 1.02 |
|  | 96.5 | 1.394 | 2.12 |

The values of the stoichiometric coefficients in the last column of the Table, which were determined from the ratio of the anionic to cationic charge concentrations by titration of the polymer samples with sodium polyacrylate, shows an increasing degree of branching with progressive polymerization conversion. The higher values of this ratio can be explained by the reduced accessibility of the cationic charge in strongly branched structures. The same situation is observed when the values of Example 8 are compared with the value of Example 6.

EXAMPLES 8–11

Examples 8–11 show the influence of the amine concentration on the polymerization results. A copolymer of acrylamide and dimethylaminopropyl methacrylamide with 10 mole % of amine units in the polymer chain was used as the polymeric amine compound. The concentration of ammonium persulfate was $2.5\times10^{-2}$ mole/L and the polymerization was carried out according to Example 1. Table 3 contains the polymerization results.

TABLE 3

Polymerization of DADMAC with polyacrylamide-co-dimethylaminopropyl-methacrylamide

| example | [polyamine]/mole · $L^{-1}$ | conversion % | intrinsic viscosity, dL × $g^{-1}$ |
|---|---|---|---|
| Example 8 | 0.01 | 88.5 | 0.896 |
| Example 9 | 0.025 | 93 | 1.165 |
| Example 10 | 0.04 | 94.5 | 1.282 |
| Example 11 | 0.07 | 97.5 | 1.375 |

The values of Table 3 illustrate the increasing tendency both of the polymerization conversion as well as of the intrinsic viscosity which is related with an excess of polyamine in comparison to the persulfate concentration.

EXAMPLES 12–15

In the following comparative examples, the influence of the persulfate concentration on the polymerization results of DADMAC polymerization is shown. A DADMAC copolymer with 11.6 mole % of dimethylaminopropyl-methacrylamide units was used as the polymeric amine compound. The concentration of the amine groups in the reaction mixture was chosen to be $2.5\times10^{-2}$ mole/L and the polymerization was carried out according to Example 1. The results of the experiments are listed in Table 4.

TABLE 4

Polymerization of DADMAC with
DADMAC-dimethylamiopropyl-methacrylamide

| Example | [persulfate]/mole/L | conversion/% | intrinsic viscosity/dL/g |
|---|---|---|---|
| Example 12 | 0.01 | 85.6 | 1.256 |
| Example 13 | 0.025 | 90.2 | 1.153 |
| Example 14 | 0.04 | 92.5 | 1.062 |
| Example 15 | 0.07 | 92.7 | 0.689 |

The values of Table 4 show the disadvantageous influence of increasing persulfate concentration on the polymerization process regarding the viscosities.

What is claimed is:

1. A water-soluble high molecular weight quaternary ammonium graft polymer prepared by grafting quaternary ammonium salt side chains onto a polyamine backbone under free radical conditions wherein the initiator system comprises a free radical-producing oxidizing agent and the polyamine backbone, wherein the graft polymer comprises from about 0.1 to about 30 mole percent polyamine backbone and from about 99.9 to about 70 mole percent quaternary ammonium salt side chains and a number average molecular weight of greater than 100,000 g/mol.

2. The graft polymer of claim 1 wherein the polyamine backbone is selected from polyampholytes, copolymers of diallyldimethylammonium chloride and a polymerizable amine compound, polyamide amines and copolymers of diallyldimethylammonium chloride and triethanolamine.

3. The graft polymer of claim 1 having a number average molecular weight of greater than 250,000 g/mol.

4. The graft polymer of claim 1 wherein the polyamine backbone has a number average molecular weight of from about 10,000 to about 100,000 2 mol.

5. The graft polymer of claim 1 wherein the quaternary ammonium salt is a diallyldimethyl ammonium halide.

6. The graft polymer of claim 2 wherein the copolymer of diallyldimethylammonium chloride and a polymerizable amine compound has formula

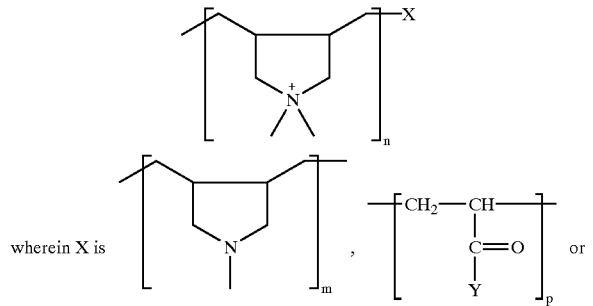

wherein X is

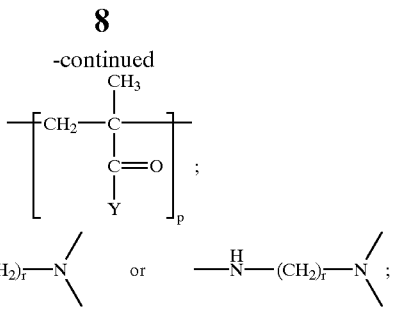

Y is —O—(CH$_2$)$_r$—N⟨ or —N(H)—(CH$_2$)$_r$—N⟨ ;

n, m and p are selected such that the copolymer has a number amine has a number average molecular weight of from about 10,000 to about 100,000; and the ratio of n:m or n:p is from about 1:1 to about 95:1; and r is 2 or 3.

7. The graft polymer of claim 2 wherein the polyamide aminehas formula

—[CH$_2$—CH$_2$—C(O)—NH—CH$_2$—HN—C(O)—CH$_2$—CH$_2$—W]$_n$—

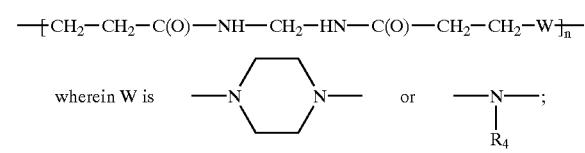

n is selected such that the polyamide amine has a number average molecular weght of from about 10,000 to about 100,000; and R$_4$ is alkyl or hydroxyalkyl.

8. The graft polymer of claim 2 wherein the polyamine backbone is a copolymer of diallydimethylammonium chloride and from about 0.5 to about 5 mole percent triethanolamine.

9. The graft polymer of claim 2 wherein the polyampholyte has formula

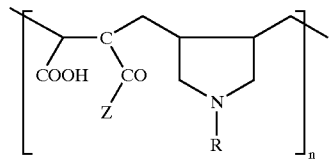

wherein Z is OH or NRR$_1$; R is H or alkyl; R$_1$ is H, alkyl or aryl; and n is selected such that the polyampholyte has a number average molecular weight of from about 10,000 to about 100,000 g/mol.

* * * * *